(12) United States Patent
Bammesberger et al.

(10) Patent No.: US 10,466,264 B2
(45) Date of Patent: Nov. 5, 2019

(54) DISPENSING ASSEMBLY

(71) Applicant: Roche Diagnostics Operations, Inc., Indianapolis, IN (US)

(72) Inventors: Stefan Borja Bammesberger, Stuttgart (DE); Andreas Ernst, Bollschweil (DE); Peter Koltay, Freiburg (DE); Nadine Losleben, Mannheim (DE); Laurent Tanguy, Freiburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 449 days.

(21) Appl. No.: 14/530,863

(22) Filed: Nov. 3, 2014

(65) Prior Publication Data

US 2015/0050719 A1    Feb. 19, 2015

Related U.S. Application Data

(63) Continuation of application No. PCT/EP2013/059492, filed on May 7, 2013.

(30) Foreign Application Priority Data

May 8, 2012    (EP) .................................... 12167107

(51) Int. Cl.
*B01L 3/02*    (2006.01)
*G01N 35/10*    (2006.01)
(Continued)

(52) U.S. Cl.
CPC ........ *G01N 35/1016* (2013.01); *B01L 3/0268* (2013.01); *B05B 17/06* (2013.01);
(Continued)

(58) Field of Classification Search
CPC ...... B01L 2200/06; B01L 3/021; B01L 3/268; G01N 35/1016
See application file for complete search history.

(56) References Cited

U.S. PATENT DOCUMENTS 4,405,344 A * 9/1983 Sisti ...................... G01N 30/16
        95/89
5,460,782 A * 10/1995 Coleman ................ B01L 3/022
        422/520

(Continued)

FOREIGN PATENT DOCUMENTS

EP    1099484 A1    5/2001
EP    1206966 A1    5/2002
(Continued)

OTHER PUBLICATIONS

International Search Report dated Aug. 6, 2013 in Application No. PCT/EP2013/059492, 4 pages.
(Continued)

*Primary Examiner* — Jonathan M Hurst
(74) *Attorney, Agent, or Firm* — Roche Diagnostics Operations, Inc.

(57) ABSTRACT

A dispensing assembly comprising a cartridge holder is presented. The cartridge holder can receive a cartridge for dispensing a fluid. The cartridge can comprise a reservoir for receiving the fluid. The reservoir can comprise an outlet. The reservoir can have an adjustable volume for forcing the fluid through the outlet. The cartridge can further comprise a nozzle for dispensing the fluid. The nozzle can be connected to the outlet. The dispensing assembly can further comprise an actuator for actuating the adjustable volume. The dispensing assembly can further comprise an impulse generator for imparting an impulse to the nozzle. The impulse generator can comprise an actor for contacting the nozzle. The dispenser assembly can further comprise a controller for controlling the actor and the impulse generator.

13 Claims, 9 Drawing Sheets

(51) Int. Cl.
  *B05B 17/06*  (2006.01)
  *B05C 5/02*  (2006.01)
  *B05B 1/02*  (2006.01)

(52) U.S. Cl.
  CPC ..... *G01N 35/1002* (2013.01); *G01N 35/1009* (2013.01); *B01L 2200/143* (2013.01); *B05B 1/02* (2013.01); *B05C 5/0225* (2013.01); *B05C 5/0291* (2013.01); *G01N 2035/1025* (2013.01)

(56) References Cited

U.S. PATENT DOCUMENTS

| | | | |
|---|---|---|---|
| 5,763,278 A | | 6/1998 | Sickinger et al. |
| 5,916,524 A | * | 6/1999 | Tisone .................. B01L 3/0265 118/305 |
| 6,203,759 B1 | * | 3/2001 | Pelc ..................... B01L 3/0265 222/333 |
| 2004/0050861 A1 | * | 3/2004 | Lisec ..................... B01L 3/022 222/57 |
| 2004/0166028 A1 | * | 8/2004 | Husar .................. B01L 3/0268 422/506 |
| 2006/0251797 A1 | * | 11/2006 | Erfle ........................ B05C 5/02 427/8 |
| 2007/0248498 A1 | * | 10/2007 | Robertson ............ B01L 3/0241 422/400 |

FOREIGN PATENT DOCUMENTS

| | | |
|---|---|---|
| EP | 1959257 A2 | 8/2008 |
| JP | 2010175291 A | 8/2010 |

OTHER PUBLICATIONS

Meinel, Andreas and Wolf, Richard, "Water Droplets on the Nano Trampoline," Jugend Forscht Online, 2008, retrieved from http://www.jugend-forscht.de/projektdatenbank/wassertrophfen-auf-dem-nano-trampolin Feb. 19, 2014, with English translation, 31 pages.

* cited by examiner

DISPENSING ASSEMBLY

CROSS-REFERENCE TO RELATED APPLICATIONS

This application is a continuation of PCT/EP2013/059492, filed May 7, 2013, which is based on and claims priority to EP 12167107.7, filed May 8, 2012, which is hereby incorporated by reference.

BACKGROUND

The present disclosure generally relates to the dispensing of fluids.

In medical laboratories, in vitro diagnostics are commonly performed on biological samples. Such tests may be performed manually using pipettes or maybe performed using an automatic analyzer. Automatic analyzers may automatically add reagents to the biological sample and may measure one or more physical properties of the biological sample during analysis.

SUMMARY

According to the present disclosure, a dispensing assembly is presented. The dispensing assembly can comprise a cartridge holder. The cartridge holder can receive a cartridge for dispensing a fluid. The cartridge can comprise a reservoir for receiving the fluid. The reservoir can comprise an outlet. The reservoir can have an adjustable volume for forcing the fluid through the outlet. The cartridge can further comprise a nozzle having an orifice for dispensing the fluid. The nozzle can be connected to the outlet. The dispensing assembly can further comprise an actuator for actuating the adjustable volume and an impulse generator for imparting an impulse to the nozzle. The impulse generator can comprise an actor for contacting the nozzle. The dispensing assembly can further comprise a controller for controlling the actuator and the impulse generator. The controller is programmed to control the actuator to force a predetermined volume of fluid through the outlet, to control the impulse generator to impart an impulse to the nozzle after the predetermined volume of fluid is forced through the outlet and/or to control the impulse generator to impart an impulse to the nozzle during the forcing of the predetermined volume fluid through the outlet Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
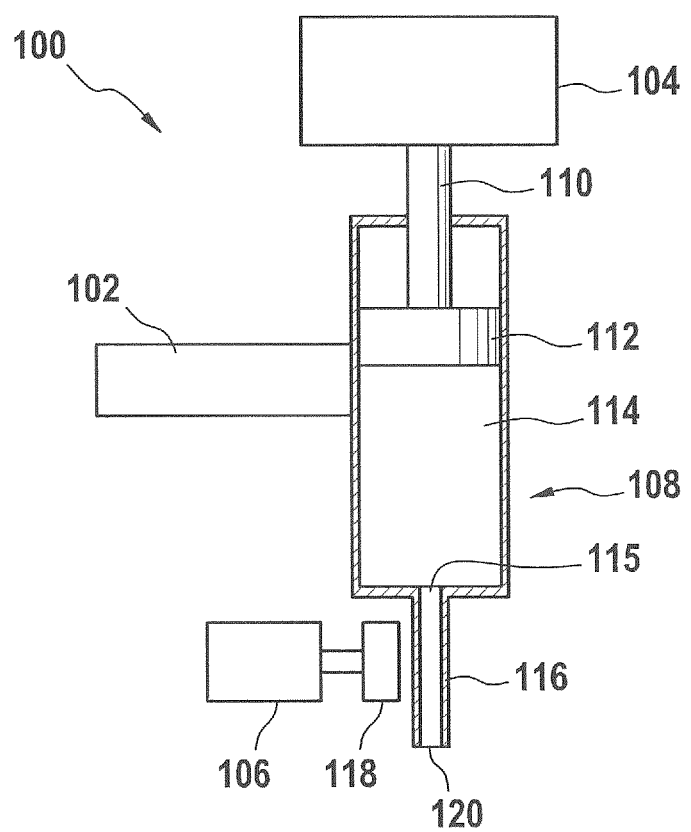
FIG. 1 illustrates a dispenser assembly according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A controller as used herein can encompass a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein can encompass any device comprising a processor. A 'processor' as used herein can encompass an electronic component which can execute a program or machine executable instruction.

A 'computer-readable storage medium' as used herein can encompass any tangible storage medium which may store instructions which can be executable by a processor of a computing device. The computer-readable storage medium may be referred to as a computer-readable non-transitory storage medium.

'Computer memory' or 'memory' can be an example of a computer-readable storage medium. Computer memory can be any memory which can be directly accessible to a processor or other controller. 'Computer storage' or 'storage' can be an example of a computer-readable storage medium. Computer storage can be any non-volatile computer-readable storage medium.

A 'user interface' as used herein can be an interface which can allow a user or operator to interact with a computer or computer system.

A 'hardware interface' as used herein can encompass an interface which can enable a processor or other controller to interact with and/or control an external computing device and/or apparatus. A hardware interface may allow a processor to send control signals or instructions to an external computing device and/or apparatus.

A dispensing assembly is provided. The dispensing assembly can comprise a cartridge holder. The cartridge holder can receive a cartridge for dispensing a fluid. The cartridge can comprise a reservoir operable for receiving the fluid. The reservoir can comprise an outlet. The reservoir can have an adjustable volume for forcing the fluid through the outlet. In some embodiments, the volume of the reservoir may be increased to suck fluid into the reservoir. In some embodiments, the volume of the reservoir may also be increased to aspirate liquid through the nozzle. This may be used for example to fill the reservoir.

The cartridge can further comprise a nozzle for dispensing the fluid. The nozzle can be connected to the outlet. The dispensing assembly can further comprise an actuator for actuating the adjustable volume. The dispensing assembly can further comprise an impulse generator for imparting an impulse to the nozzle. This embodiment may be beneficial because it may provide a method for dispensing the fluid more accurately. The impulse generator may be able to knock droplets or drops out of the nozzle or off of the nozzle to make the dispensing more reliable and more reproducible.

The impulse generator may take different forms depending on how it is constructed. It may be a piezoelectric actuator and may use such things as a piston or ring for actuating the nozzle. The impulse generator may be pneumatically actuated; this may include a concentric nozzle or a fan jet. The actuator may be an electromagnetically actuated piston and plunger, for example, a hard magnet inside of a coil. The impulse generator may further be a piston and plunger actuated by a linear drive or a motor of some sort. The impulse generator may further be an acoustic or ultrasonic impulse generator.

The term "actor" as understood herein can relate to a mechanical contact element that can be driven to mechanically act upon another element, for example, the elastomeric fluid conduit, by exercising a mechanical force.

The impulse generator can comprise an actor for contacting the nozzle. The actor may be used for imparting the impulse to the nozzle. The impulse can be communicated from the impulse generator directly to the nozzle. Imparting the impulse directly to the nozzle as is done in the present disclosure may reduce the amount of force needed to knock a drop from the nozzle. This may be particularly beneficial when the fluid to be dispensed is sensitive to shear forces.

The actuator may take several different forms. In one embodiment, the actuator can be a syringe pump. However, other such sorts of pumps such as, for example, peristaltic pump, a diaphragm pump or other pressure-generating system may also be used. In some embodiments, the cartridge can comprise a plunger, however this is not necessary. There can be no plunger at all or the plunger can be part of the actuator.

In another embodiment, the nozzle can be a flexible nozzle.

In another embodiment, the dispensing assembly can further comprise a meniscus detector for detecting a meniscus of the fluid.

In another embodiment, the cartridge can further comprise a piston. The piston can change the volume of the reservoir and force the fluid through the outlet.

In another embodiment, the dispensing assembly can further comprise a controller for controlling the actuator and the impulse generator.

In another embodiment, the dispensing assembly can further comprise a meniscus detector for detecting the meniscus of the fluid. The controller can be programmed to control the actuator to force the fluid through the outlet. The controller can further be programmed to detect the meniscus using the meniscus detector. The controller can further be programmed to control the actuator to halt the forcing of the fluid through the outlet when the meniscus is in a predetermined location. This embodiment may be beneficial because if the meniscus is in the same place when the fluid dispensing starts, then the dispensing of the fluid may be more accurate, more precise and/or more reproducible. The meniscus may be inside or outside the nozzle. For instance, the nozzle may be a long tube-like structure and the meniscus may have a particular position within the tube. In other embodiments, the meniscus may be formed by a drop of the fluid hanging from the nozzle. So in this case, the meniscus may therefore be inside or outside the flexible nozzle. In many applications, the meniscus can be positioned right at the orifice of the nozzle.

In another embodiment, the controller can further be programmed to control the actuator to force a predetermined volume of fluid through the outlet. In some embodiments, the actuator may be controlled to force the predetermined volume after the meniscus is in the predetermined location. The controller can further be programmed to control the impulse generator to impart an impulse to the nozzle after the predetermined volume of fluid is forced through the outlet. This embodiment may be beneficial because it may be used to knock or remove fluid from the nozzle in a controllable and defined fashion; after dispensing this may make the dispensing of the fluid more accurate and more reproducible.

In another embodiment, the impulse generator can be control to impart a predetermined number of impulses of defined duration and force to the nozzle.

In another embodiment, the controller can further be programmed to control the actuator to force a predetermined volume of fluid through the outlet. In some embodiments, the predetermined volume of fluid may be forced through the outlet after the meniscus is in the predetermined location. The controller can further be programmed to control the impulse generator to impart an impulse to the nozzle during the forcing of the predetermined volume of fluid through the outlet and, also after the predetermined volume of fluid can be forced through the outlet. In this embodiment, an impulse can be directed towards the nozzle during and after dispensing of the fluid.

In another embodiment, the controller can further be programmed to control the actuator to force a predetermined volume of fluid through the outlet. In some embodiments, the actuator may be controlled to force the predetermined volume of fluid through the outlet after the meniscus is in the predetermined location. The controller can further be programmed to control the impulse generator to impart an impulse to the nozzle during the forcing of the predetermined volume of fluid through the outlet.

In another embodiment, the controller can further be programmed to control the actuator to withdraw a second predetermined volume of fluid through the outlet from the nozzle after controlling the impulse generator to impart the impulse. This embodiment may be beneficial because it may be used to withdraw fluid from the nozzle further into the nozzle or even back into the reservoir.

In another embodiment, the meniscus detector can be any one of the following: a capacitive sensor, an optical sensor or a camera. When the meniscus is inside of the nozzle, a capacitive sensor may be used to detect the location of the meniscus. In case the nozzle is optically transparent, an optical sensor may also be used to determine the location of the meniscus within the nozzle. If the meniscus extends beyond the nozzle, then a capacitive sensor, an optical sensor or a camera may each be used to determine the location of the meniscus.

In another embodiment, the nozzle can be a flexible nozzle and the dispensing assembly can further comprise a valve for compressing the flexible nozzle at a compression location. This embodiment may be beneficial because it can enable the flexible nozzle to be sealed. This may prolong the lifetime of the fluid within the reservoir. In some embodiments, the valve can be a pinch valve.

In another embodiment, the nozzle may receive a cap for sealing it.

In another embodiment, withdrawing the second predetermined volume of the fluid can cause the meniscus to withdraw to a withdrawal location within the flexible nozzle. The flexible nozzle can have an orifice. The compression location can be between the withdrawal location and the orifice. This embodiment may be beneficial because all of the fluid can be withdrawn such that it can be sealed by the valve.

In another embodiment, the impulse generator can comprise an actor for contacting the nozzle. The actor may be used for imparting the impulse to the nozzle or may be considered to attach or detach the impulse generator to the nozzle.

In another embodiment, the impulse generator can be in contact or permanent contact with the nozzle. When impulse generator generates an impulse, it can cause the actor to move which, in turn, can impart an impulse to the nozzle. This impulse can cause the nozzle to move also. In this embodiment, the actor can cause a brief momentary displacement of the nozzle.

Since the actor is already in contact with the nozzle, there can be no impact. The imparting of the impulse without an impact may be beneficial if the fluid has a delicate component such as stem cells. In some embodiments, the impulse generator can cause the actor to move approximately 30 µm.

In another embodiment, the dispensing assembly can further comprise a linear translator for placing the actor in contact with the nozzle. For example, the linear translator may move the entire impulse generator and the actor such that the actor can be in contact with the nozzle. A translation table can, for example, have a range of movement of about 20 mm.

In another example, the linear translator can be a part which can expand or contract between the impulse generator and the actor such that the impulse generator can remain in a fixed position as the actor can be positioned to be in contact with the nozzle.

In another embodiment, the meniscus detector can be located between the orifice and the actor.

In another embodiment, there can be a first distance between the meniscus detector and the orifice to prevent contamination of the meniscus detector when dispensing the fluid.

In another embodiment, there can be a second distance between the meniscus detector and the actor to prevent motion of the actor from affecting operation of the meniscus detector.

In another embodiment, the meniscus detector can measure the meniscus location within the nozzle. For example, the side walls of the nozzle can be transparent and the meniscus detector may be optical. In other embodiments, the meniscus detector may be a capacitive detector.

In another embodiment, the actor can move approximately 30 micrometers when receiving an impulse from the impulse generator. For example, when the actor is already in contact with the nozzle, it may receive an impulse which can cause the actor and the nozzle to move about 30 micrometers.

In another embodiment, the nozzle can form a channel or is a tube. In one example, the reservoir can have an inner diameter of approximately 500 micrometers, 200 micrometers, or 1 mm in diameter. The cross section of the nozzle may not be circular.

In another embodiment, the nozzle can have a side wall. The actor can transfer the impulse of the impulse generator to the side wall. This embodiment may be beneficial because it may require a low force to knock any droplets off of the nozzle. In some cases, the fluid may contain fragile structures which can be damaged by large impacts. If the actor and the side wall are in contact before the impulse is generated, then the nozzle can be moved without an impact from the actor.

In another embodiment, the impulse generator can impart an impulse to the nozzle by impacting the nozzle with the actor.

In another embodiment, the nozzle can be formed from a plastic. This embodiment may be beneficial because the nozzle can be extremely light and therefore can require less force to knock a droplet off than other materials such as metal or glass.

In another embodiment, the nozzle can dispense the fluid in a first direction. The actor can contact the nozzle with motion in a second direction. The first direction can be transverse or almost transverse to the second direction. This embodiment may be beneficial because applying the impulse transverse to the direction of dispensing may reduce the shear forces necessary to knock a droplet free.

In one example, the first direction can be vertical or mostly vertical in an operating position of the dispensing assembly. In this case, the second direction can be horizontal or mostly horizontal.

In another embodiment, the dispenser can be a microfluidic dispensing assembly.

In another embodiment, the dispensing assembly can dispense any one of the following volumes: less than 10 ml, less than 5 mL, less than 1 mL, less than 10 µL, less than 500 nL, less than 200 nL, less than 100 nL, or less than 20 nL.

In another embodiment, the dispensing assembly can comprise the cartridge.

In another embodiment, the cartridge can comprise the fluid.

In another embodiment, the fluid comprises a reagent, a blood grouping reagent, a solvent, a diluent, a catalyst, an antibody, an enzyme, a recombinant protein, a virus isolate, a virus, a biological reagent, a protein, a salt, a detergent, a nucleic acid, an acid, a base or combinations thereof.

In another embodiment, the fluid can comprise a dispersion such as a dispersion of particles within the fluid.

In another embodiment, the fluid can comprise latex particles, nanoparticles, magnetic particles, stem cells, cells, biological structures, microorganisms of combinations thereof.

In another embodiment, the cartridge can comprise a syringe. For instance, the syringe may be connected to a nozzle and a syringe pump may be used as the actuator for actuating the syringe.

In another embodiment, the actuator can be a syringe pump.

An automatic analyzer can be provided. The automatic analyzer can be for analyzing the biological sample comprising a dispensing assembly.

Referring initially to FIG. 1, FIG. 1 illustrates a dispenser assembly 100. The dispensing assembly 100 can comprise a cartridge holder 102, an actuator 104 and an impulse generator 106. The cartridge holder 102 is shown as being attached to a cartridge 108. The actuator 104, in this example, is shown as having a plunger 110 in contract with a piston 112. The plunger 110 and piston 112 may not be present in all embodiments. Depending upon the implementation the plunger 110 and/or the piston 112 can be components of the dispenser assembly 100 or the cartridge 108. The cartridge 108, in this embodiment, can have a reservoir 114 whose size can be controlled by the piston 112. Moving the piston 112 can make the reservoir 114 larger or smaller. The reservoir 114 can have an outlet 115 into a nozzle 116. The impulse generator 106 can have an actor 118 which can be able to come in physical contact with the nozzle 116. The piston 112 can be able to be depressed to force fluid from the reservoir 114 through the nozzle 116. This can enable fluid to be forced out of an orifice 120 in the nozzle 116. The impulse generator 106 can be able to use the actor 118 to physically contact the nozzle 116 to knock droplets out of the nozzle 116.

Figure 2:
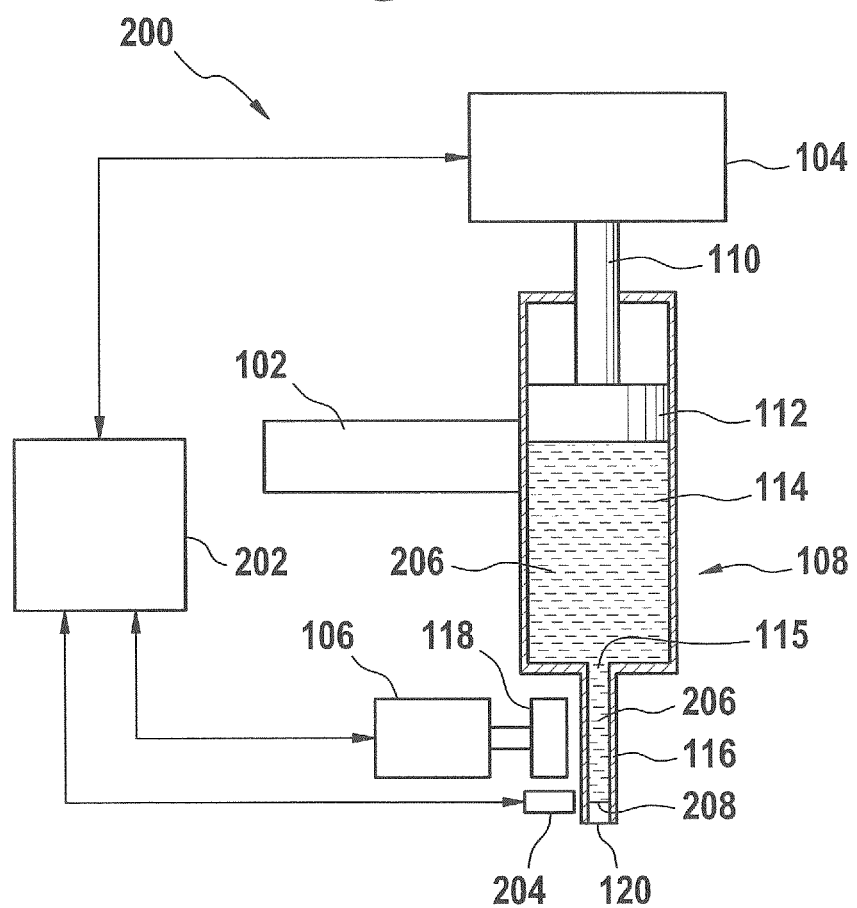
FIG. 2 illustrates a dispenser assembly according to another embodiment of the present disclosure.

FIG. 2 shows a further example of a dispenser assembly 200. This embodiment is similar to that shown in FIG. 1 except in this case, the dispenser assembly 200 can further comprise a controller 202 and a meniscus detector 204. The controller 202 can be a controller or other control apparatus which can be adapted for controlling the actuator 104, the impulse generator 106 and the meniscus detector 204. The meniscus detector 204 can be adapted for detecting a meniscus 208 in the nozzle 116. The reservoir 114 and the nozzle 116 are shown as containing a fluid 206. With the meniscus detector 204, the controller 202 can be able to control the actuator 104 such that the piston 112 can be depressed the right amount to position the meniscus 208 in a precise location. Doing this before beginning the dispensing process, the dispenser apparatus 200 can be able to more accurately dispense the proper amount of fluid 206.

In FIG. 2, the meniscus detector 204 is illustrated by a small box to one side of the nozzle 116. This representation of the meniscus detector 204 is intended to be representative. For example, if the meniscus detector were a capacitive detector, the meniscus detector 204 may surround all or a portion of the nozzle 116.

Figure 3:
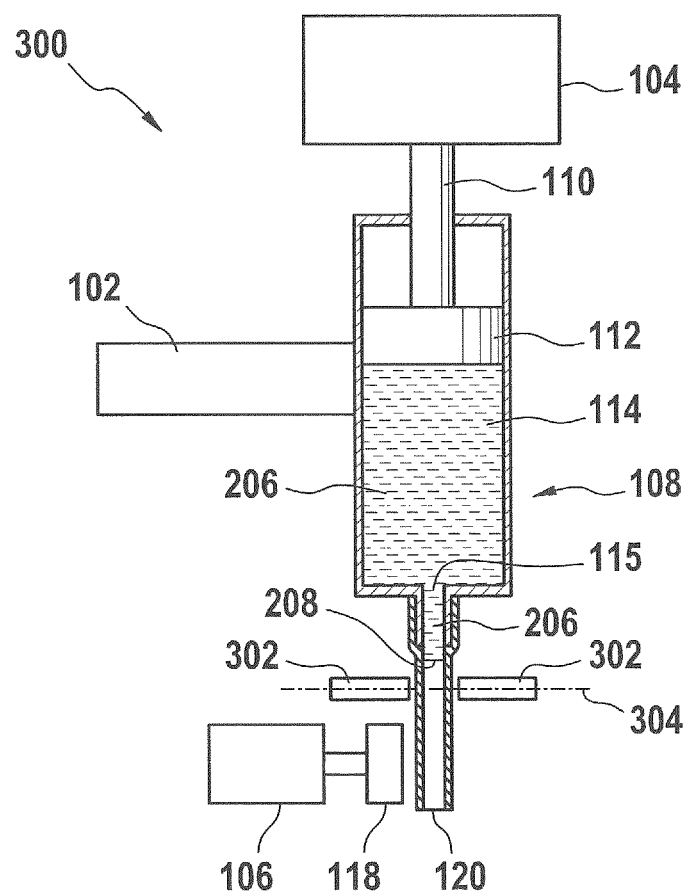
FIG. 3 illustrates a dispenser assembly according to yet another embodiment of the present disclosure.

FIG. 3 shows a dispenser assembly 300. The embodiment shown in FIG. 3 is similar to that shown in FIGS. 1 and 2. In this embodiment, the dispenser assembly 300 can comprise a pinch valve 302 and the nozzle 116 can be flexible. The pinch valve 302 can be adapted for squeezing and pinching closed the flexible nozzle 116 at a compression location 304. This location at which the pinch valve closes the flexible nozzle 116 is marked by the dashed line. In this example, it can be seen that the compression location 304 can be between the orifice 120 and the fluid meniscus 208. When the pinch valve 302 closes, the entire volume of the fluid 206 can be sealed from the atmosphere.

In FIG. 3, the representation of the pinch valve 302 by 2 rectangles is intended to be representative. Different sorts of mechanisms can be used to function as a pinch valve 302. For instance, the pinch valve 302 may be a single movable piece which can press or compress the flexible nozzle 116 against a stationary object.

Figure 4:
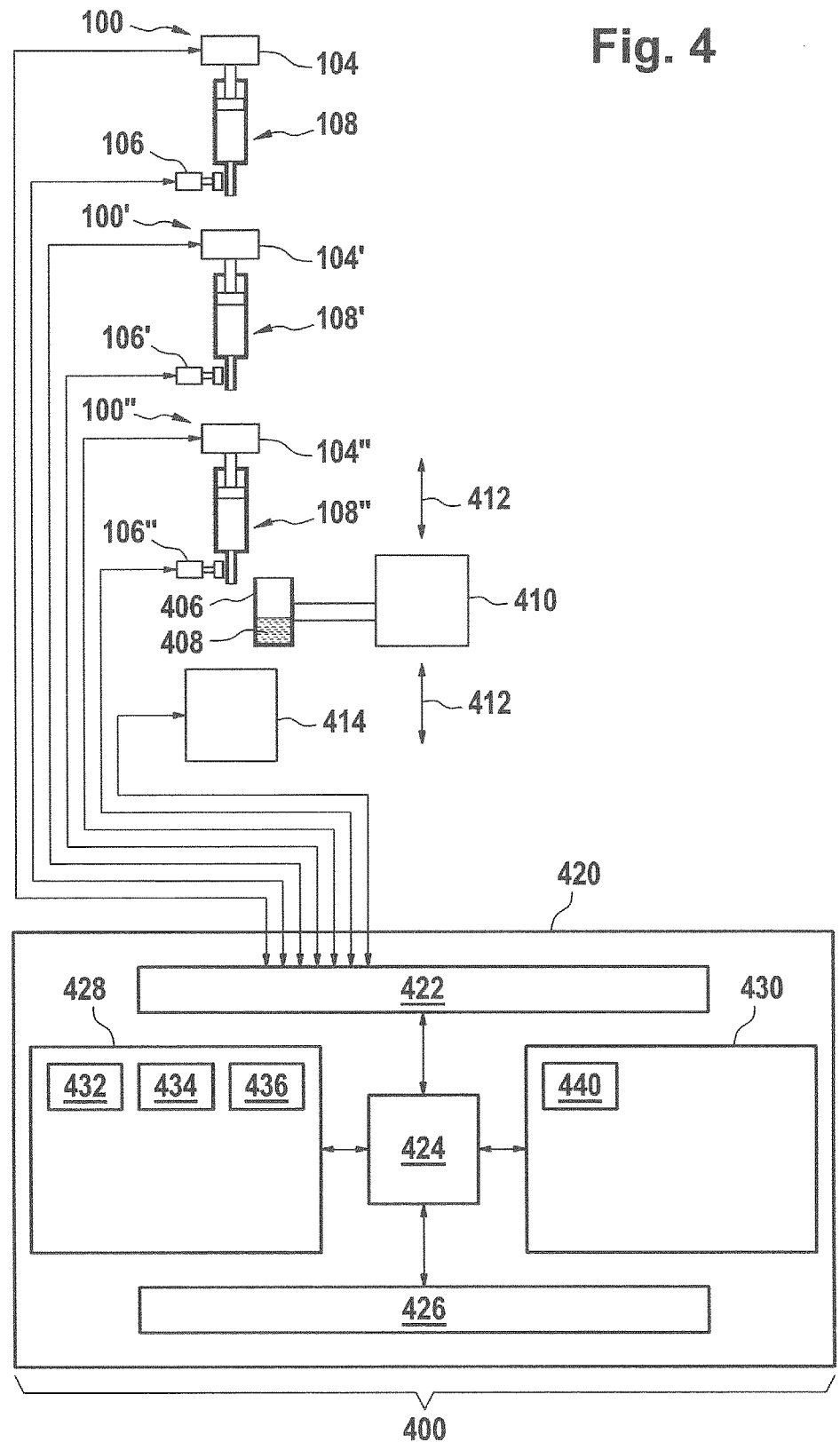
FIG. 4 illustrates an automatic analyzer according to an embodiment of the present disclosure.

FIG. 4 illustrates an automatic analyzer 400. This automatic analyzer is shown as having three cartridges 108, 108' and 108". There can be a dispenser assembly 100 connected to cartridge 108. There can be a dispenser assembly 100' attached to cartridge 108'. There can be a dispenser assembly 100" attached to cartridge 108". The dispenser assemblies 100, 100', and 100" can be equivalent to the dispenser assembly 100 shown in FIG. 1. However, not all components of the dispenser assembly are detailed in FIG. 4.

The automatic analyzer 400 is shown as having a relative mover 410 which can provide relative movement 412 between a sample holder 406 and the cartridges 108, 108' and 108". The sample holder 406 is shown as containing a biological sample 408. The cartridges 108, 108', 108" may be used to add one or more fluids to the biological sample 408. The automatic analyzer 400 is shown as further containing a sensor system 414. The sensor system can comprise one or more sensors for measuring a physical quantity or physical property of the biological sample 408. For example, the sensor system 414 may comprise an NMR system, an optical transmission or reflectance measurement system, a spectrometric measurement system, an electrochemical or optical sensor, a pH meter, a camera system, and a chromatography system. The relative mover 410 can also move the sample holder 406 to the sensor system 414.

The arrangement of the cartridges 108, 108', 108" and the sensor system 414 is representative. In some embodiments, the sample holder 406 may remain in a fixed position and the cartridges 108, 108', 108" may move. Each cartridge 108, 108', 108" is shown as being installed in a dispenser assembly 100, 100', 100".

The dispenser assemblies 100, 100', 100" can each comprise an impulse generator 106, 106', 106" and an actuator 104, 104', 104". The impulse generators 106, 106', 106", the actuators 104, 104', 104", and the sensor system 414 are shown as being connected to a hardware interface 422 of a computer system 420. The computer system 420 can function as a controller for the automatic analyzer 400. The computer 420 is further shown as containing a processor 424 which can control the operation and function of the automatic analyzer 400 using the hardware interface 422. The processor 424 is shown as further being connected to a user interface 426, computer storage 428 and computer memory 430. The computer storage 428 is shown as containing an analysis request 432. The analysis request 432 can contain a request to analyze the biological sample 408.

The computer storage 428 is shown as further containing sensor data 434 received from the sensor system 414. The computer storage 428 is shown as further containing an analysis result 436 which can be determined using the sensor data 434. The computer memory 430 can contain a control module 440. The control module 440 can contain computer executable code which can enable the processor 424 to control the operation and function of the automatic analyzer 400. For instance, the control module 440 may use the analysis request 432 to generate commands to generate and send to the dispenser assemblies 100, 100', 100", the sensor system 414 and the relative movement system 410. The control module 440 may also generate the analysis result 436 using the sensor data 434.

Figure 5:
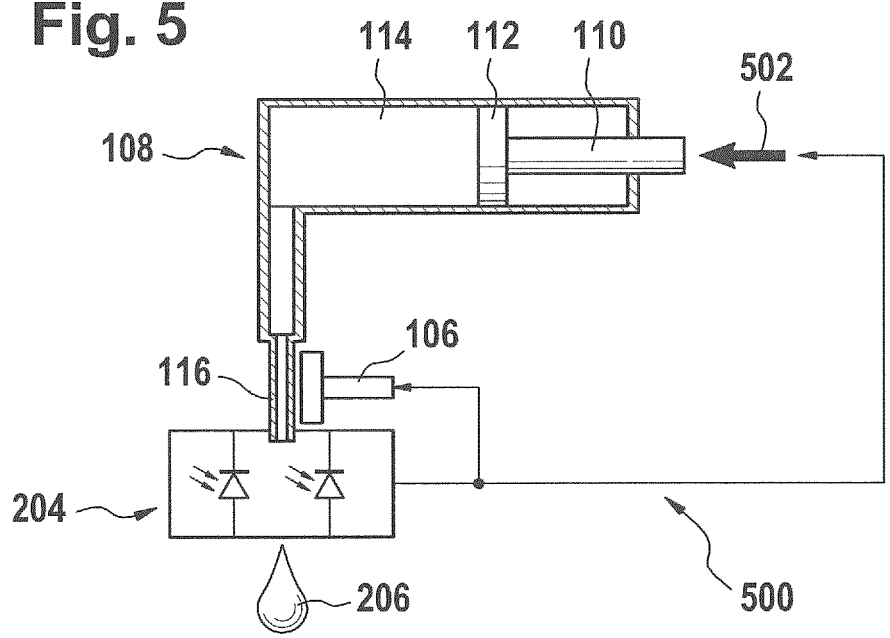
FIG. 5 illustrates a dispenser assembly according to still another embodiment of the present disclosure.

FIG. 5 shows a functional diagram of a dispenser assembly. The embodiment shown in FIG. 5 is similar to that shown in FIGS. 1, 2 and 3. In this example, a syringe pump 502 can be used as the actuator. In this example, an optical detector can be used as the meniscus detector 204, it may also be used to measure droplets of fluid 206 exiting from the nozzle 116.

Figure 6:
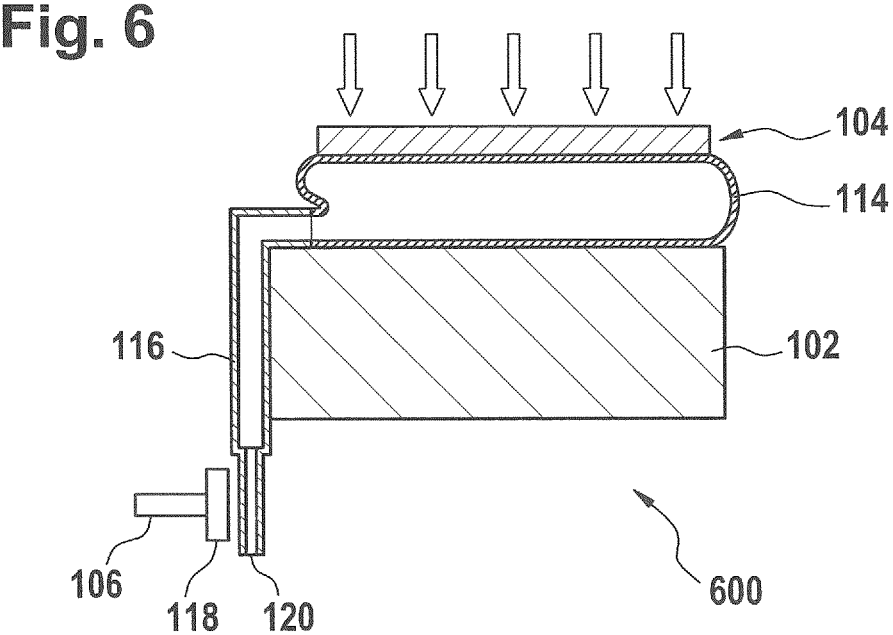
FIG. 6 illustrates a dispenser assembly according to another embodiment of the present disclosure.

FIG. 6 shows a dispenser assembly 600. In this embodiment, there can be a reservoir 114 that can be bag-like and the actuator 104 can exert pressure directly on the reservoir 114 to force liquid out of the orifice 120. The bag-like reservoir 114 can be squeezed between the actuator 104 and the cartridge holder 102.

Figure 7:
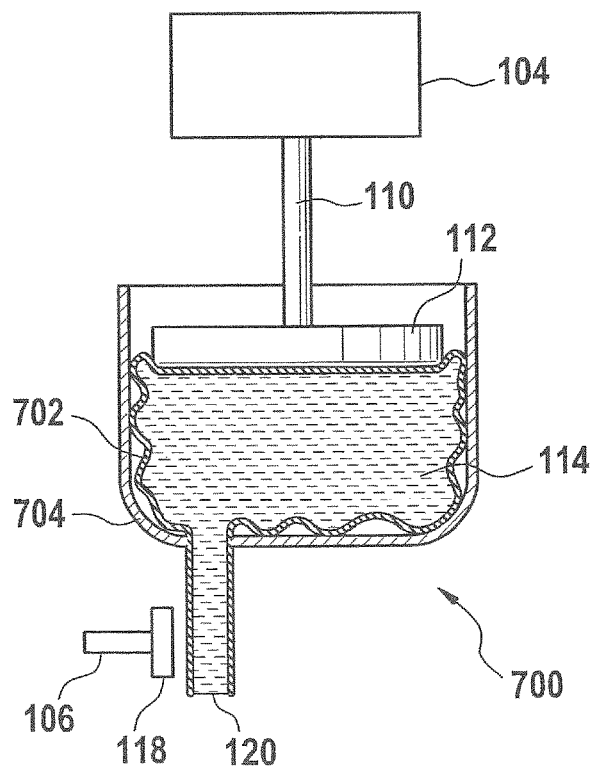
FIG. 7 illustrates a dispenser assembly according to a further embodiment of the present disclosure.

FIG. 7 shows a dispenser assembly 700. This embodiment is similar to the embodiments shown in FIGS. 1, 2, 3 and 5. In this case, the reservoir 114 can be formed by a bag 702 which can be contained within a bag support 704. The plunger 112 can be used to compress the bag 702 and force fluid out of the orifice 120.

Figure 8:
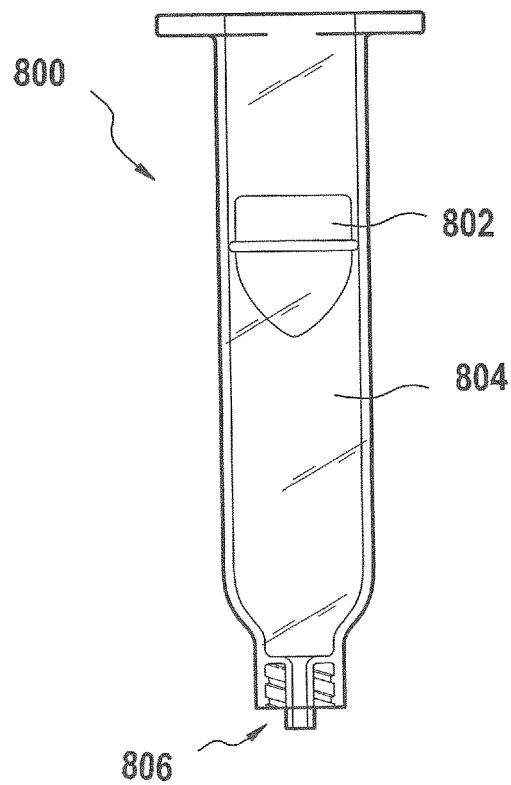
FIG. 8 illustrates an example of a tube and a piston which are used to form a reservoir according to an embodiment of the present disclosure.

FIG. 8 shows an example of a tube 800 and a piston 802 which can be used to form a reservoir 804. The reservoir 804 can have an outlet 806. In this embodiment, the piston 802 can be actuated by a plunger attached to an actuator. In this embodiment the outlet 806 is shown as have a Luer-Lock connection.

Figure 9:
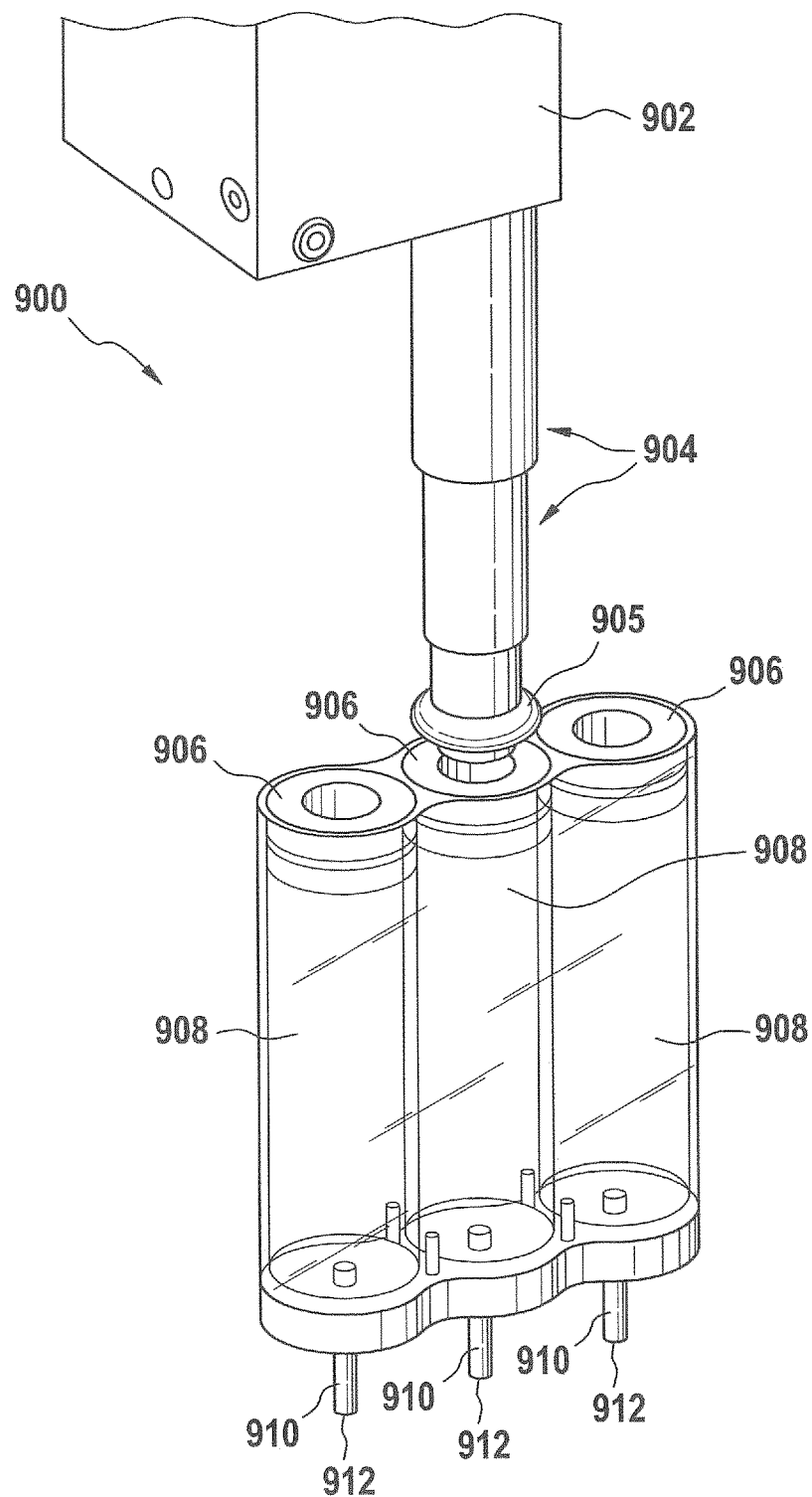
FIG. 9 illustrates a dispenser assembly according to another embodiment of the present disclosure.

FIG. 9 illustrates a further example of a dispenser assembly 900. In this embodiment, there can be a syringe pump 902 which can function as the actuator 104. There can be a plunger 904 which can be actuated by the syringe pump 902. The inflatable gripper 905 on the end of the plunger 904 can be able to grab pistons 906 each of which can be mounted at the end of the reservoirs 908. The plunger 904 can then be able to move a piston back and forth to change the volume of the reservoir 908. At the bottom of the reservoir 908 can be a nozzle 910 with an orifice 912 through which fluid can be forced out of. As an alternative to the inflatable gripper 905, other types of grippers; for example, holding the piston by vacuum, electromagnetic holding systems, and the like can be used.

In another embodiment, a robotic arm can move the cartridge from a parking to a dispensing position and vice versa.

In another embodiment, a contact or distance sensor can be integrated into the plunger to detect the distance to the piston when the piston can be contacted by the plunger. If the plunger is part of the cartridge, a finger gripper with a contact sensor can be added to contact the plunger.

In another embodiment, the impulse generator may be put in contact with the nozzle before an impulse can be generated by the impulse generator. After the dispensing process, the impulse generator may be removed to a sufficient distance in order to be able to remove the cartridge without touching the impulse generator with the orifice or the reagent. This may help to eliminate or reduce cross contamination. For this automation purpose, an additional actor may be beneficial. For example, a pneumatic linear actuator may be used.

Figure 10:
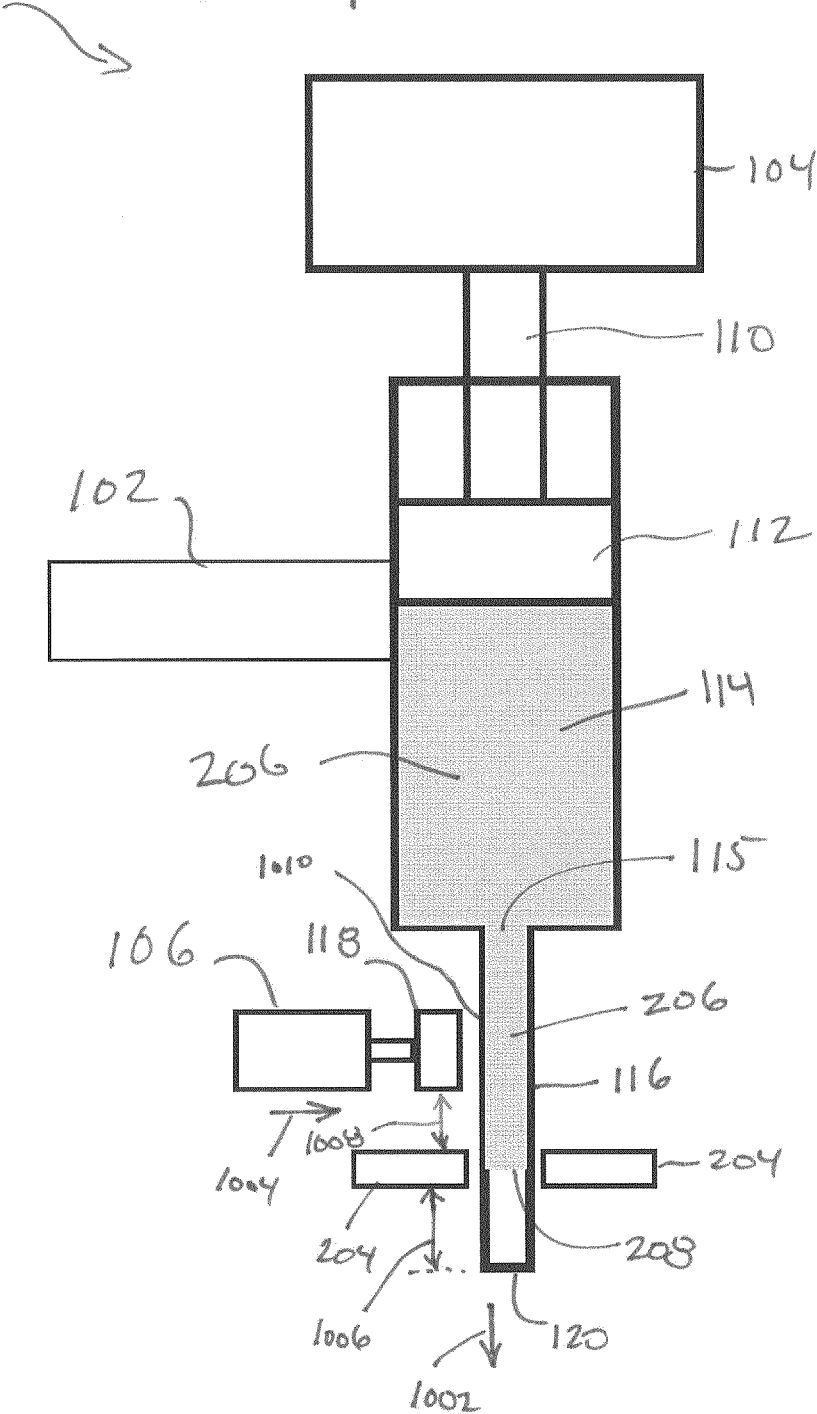
FIG. 10 illustrates a dispenser assembly which is similar to the dispenser assembly shown in FIG. 2 according to an embodiment of the present disclosure.

FIG. 10 shows a dispenser assembly 1000 which is similar to the dispenser assembly shown in FIG. 2. The dispenser assembly 1000 may also have a controller, but it is not shown in this figure. For example, the dispense assembly may have a controller 202 as is shown in FIG. 2 or a controller 420 as is shown in FIG. 4.

The meniscus detector 204 is shown as surrounding the nozzle 116. The dispenser assembly 1000 can dispense the fluid in a first direction 1002. For instance, the dispenser may dispense the fluid in a downward vertical direction. The actor 118 can move in the direction 1004. The direction 1002 and the direction 1004 are shown as being transverse or approximately transverse to each other. The meniscus detector 204 can be a first distance 1006 from the orifice 120. Placing the meniscus detector 204 at the first distance 1006 can prevent fluid 114 which is been dispensed from contacting the meniscus detector 204.

In some examples, the actor 118 may be in contact with a sidewall 1010 of the nozzle 116 before the impulse generator 106 generates the impulse.

The meniscus detector 204 can be placed at a second distance 1008 from the actor 118. This can be done so that when the actor 118 can be contacting the sidewall 1010 of the nozzle 116 the motion of the actor may not interfere with the operation of the meniscus detector 204. The arrangement shown in FIG. 10 may be particularly beneficial if the nozzle 116 is constructed of a material such as plastic. The actor 118 can contact the nozzle 116 directly. This can mean that not much force may need to be transferred to the nozzle 116 in order to knock droplets off the orifice 120. If the fluid 114 contains a component which may be damaged due to high shear forces, for example, stem cells, this arrangement may help reduce the risk of damaging those components. If, for instance, forces were applied to the entire assembly 1000 or to the plunger 110, a larger amount of force may be needed to transfer in order to knock a droplet off the orifice 120.

Figure 11:
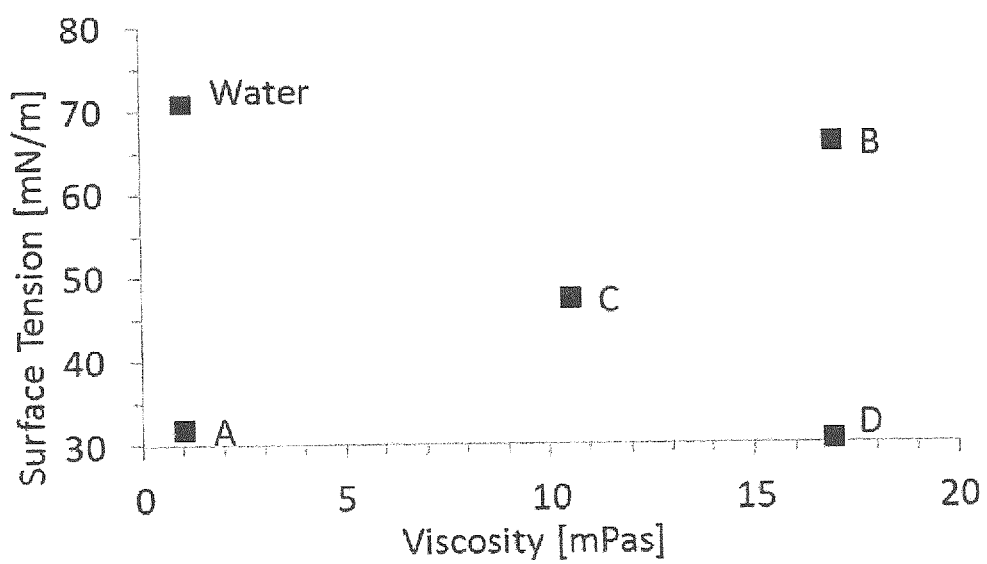
FIG. 11 illustrates a plot of the viscosity versus surface tension for several different

FIG. 11 shows a plot of the viscosity versus surface tension for several different fluids used as test liquids. Table 1 lists these fluids along with the viscosity, the surface tension, and the density for each of the fluids.

TABLE 1

| Model Fluid | Viscosity/ mPas | Surface Tension/ mN/m | Density/ kg/m$^3$ |
|---|---|---|---|
| A | 1.0 | 31.9 | 998 |
| B | 16.9 | 65.9 | 1169 |
| C | 10.5 | 47.3 | 1139 |
| Water | 1.0 | 70.8 | 998 |
| D | 16.9 | 30.5 | 1169 |

The tests liquids in table 1 cover the typical range of viscosities, surface tensions and densities of reagents that are typically used for in-vitro diagnostics. To evaluate the dispensing performance for liquids of different viscosities and surface tensions the fluids shown in FIG. 11 and Table 1 were characterized using an example of a dispensing assembly as described herein. The actuation parameters of the syringe and the impulse generator were not changed for any of the liquids. This can mean that no specific calibration of the system was performed for each individual fluid.

Table 2 shows the coefficient of variation (CV) and the accuracy (Acc) obtained with the test liquids for 2 different target volumes (1 μL and 25 μL).

TABLE 2

| Fluid → | | Water | A | B | C | D |
|---|---|---|---|---|---|---|
| CV | 1 μL | 0.9% | −1.9% | 1.8% | 1.8% | 1.3% |
| Acc | 1 μL | −3.4% | −8.8% | −1.0% | 0.3% | −1.3% |
| CV | 25 μL | 2.1% | 3.7% | 0.7% | 3.4% | 0.7% |
| Acc | 25 μL | 0.5% | −0.9% | 0.6% | −1.2% | −0.3% |

As can be seen in Table 2, the dispensing performance was as precise for the test liquids as it was for water. The CV was below 4% for all liquids. The accuracy ranged in between 0.3% at 1 μL for liquid C to 8.8% at 1 μL for liquid A. Table 2 illustrates a potential benefit of examples of the dispensing assembly when dispensing micro fluidic quantities of fluid. The variation and accuracy in the dispensing of the fluid can essentially be independent of the rheological properties of the respective fluid. Such a dispensing assembly can therefore be useful when a variety of different fluids showing different rheological properties needs to be dispensed in very small micro fluidic quantities. For example, in an automatic analyzer there may be different cartridges which dispense a variety of reagents. It may be beneficial to use an example of a dispensing assembly as described herein because it may not be necessary to calibrate for each particular reagent.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A dispensing assembly, the dispensing assembly comprising:
   a cartridge holder, wherein the cartridge holder receives a cartridge for dispensing a fluid, wherein the cartridge comprises a reservoir for receiving the fluid, wherein the reservoir comprises an outlet, wherein the reservoir has an adjustable volume for forcing the fluid through the outlet, wherein the cartridge further comprises a nozzle having an orifice for dispensing the fluid, wherein the nozzle is connected to the outlet;
   an actuator for actuating the adjustable volume;
   an impulse generator for imparting an impulse to the nozzle, wherein the impulse generator comprises an actor for contacting the nozzle and wherein the actor is in contact with the nozzle;
   a meniscus detector for detecting a meniscus of the fluid, wherein the meniscus detector is located between the orifice and the actor and wherein the meniscus detector is configured to detect the meniscus in the nozzle; and
   a controller programmed to control the actuator to force a predetermined volume of fluid through the outlet into the nozzle, to control the actuator to force fluid through the outlet, to detect the meniscus using the meniscus detector, and to control the actuator to halt the forcing of fluid through the outlet when the meniscus is in a predetermined location, wherein the controller is further programmed to control the impulse generator to impart an impulse to the nozzle after the predetermined volume of fluid is forced through the outlet and/or control the impulse generator to impart an impulse to the nozzle during the forcing of the predetermined volume fluid through the outlet.

2. The dispensing assembly according to claim 1, wherein the meniscus detector is any one of the following: a capacitive sensor, an optical sensor, or a camera.

3. The dispensing assembly according to claim 1, wherein the controller is programmed to control the actuator to withdraw a second predetermined volume of fluid through the outlet from the nozzle after controlling the impulse generator to impart the impulse.

4. The dispensing assembly according to claim 1, wherein the nozzle is formed from a plastic.

5. The dispensing assembly according to claim 1, wherein the nozzle dispenses the fluid in a first direction, wherein the actor contacts the nozzle with motion in a second direction, and wherein the first direction is transverse to the second direction.

6. The dispensing assembly according to claim 1, wherein the dispensing assembly is a micro-fluidic dispensing assembly.

7. The dispensing assembly according to claim 1, further comprises,
   a valve for sealing the nozzle at a sealing location.

8. The dispensing assembly according to claim 7, wherein withdrawing a second predetermined volume of fluid causes a meniscus of the fluid within nozzle to withdraw to a withdrawal location, and wherein the sealing location is between the withdrawal location and the orifice.

9. The dispensing assembly according to claim 1, wherein the dispensing assembly comprises the cartridge.

10. The dispensing assembly according to claim 1, wherein the fluid comprises any one of the following: a reagent, a blood grouping reagent, a solvent, a diluent, a catalyst, an antibody, an enzyme, a recombinant protein, a virus isolate, a virus, a biological reagent, a protein, a salt, a detergent, a nucleic acid, an acid, a base, a dispersion, latex particles, nano particles, magnetic particles, stem cells, cells, a biological structure, a microorganism, and combinations thereof.

11. The dispensing assembly according to claim 1, wherein the cartridge comprises a syringe.

12. An automatic analyzer for analyzing a biological sample comprising a dispensing assembly according to claim 1.

13. The dispensing assembly according to claim 1, wherein the meniscus detector is a capacitive detector configured to surround at least a portion of the nozzle.

* * * * *